United States Patent [19]

Danby

[11] Patent Number: 5,199,852

[45] Date of Patent: Apr. 6, 1993

[54] PUMPING ARRANGEMENT FOR INTRAVENOUS SUPPLY OF FLUIDS

[75] Inventor: Hal C. Danby, Sudbury, England

[73] Assignee: Danby Medical Limited, Earls Colne, England

[21] Appl. No.: 834,384

[22] Filed: Feb. 12, 1992

[30] Foreign Application Priority Data

Feb. 14, 1991 [GB] United Kingdom ............... 9103165

[51] Int. Cl.[5] .............................................. F04B 49/06
[52] U.S. Cl. ..................................... 417/26; 417/474;
417/478; 417/479
[58] Field of Search .................. 417/26, 28, 474, 478,
417/479; 604/153

[56] References Cited

U.S. PATENT DOCUMENTS 3,901,231  8/1975  Olson .
4,479,761  10/1984  Bilstad et al. ........................ 417/479
4,657,490  4/1987  Abbott ................................. 417/478
5,039,279  8/1991  Natwick et al. ..................... 417/479

Primary Examiner—Richard A. Bertsch
Assistant Examiner—David W. Scheuermann
Attorney, Agent, or Firm—Oblon, Spivak, McClelland, Maier & Neustadt

[57] ABSTRACT

A pumping arrangement including a squeezing device for deforming a length of pliant p.v.c. tubing first in one direction locally to reduce its volume and in another tending to restore its original cross-section and, on either side of squeezing device, inlet and outlet valves which operate by occluding the tubing. The squeezing device and the valves are controlled by a microprocessor control unit such that inlet valve is open and outlet valve shut while the squeezing device is relaxed and thereafter outlet valve is open and inlet valve shut while the squeezing device is operated to deform the tubing, this sequence repeating. Downstream of the output valve is a pressure responsive device providing input to the control unit whereby upon a rise in pressure in the delivery portion of tubing due to a restriction, the squeezing device is disabled and valves are open together to allow excess fluid to pass back towards the fluid source.

20 Claims, 3 Drawing Sheets

5,199,852

PUMPING ARRANGEMENT FOR INTRAVENOUS SUPPLY OF FLUIDS

BACKGROUND OF THE INVENTION

1. Field of the Invention

This invention relates to pumping arrangements and in particular to pumping arrangements for use in medical applications such as the intravenous supply of fluids to a patient.

This case also relates to the subject matter disclosed is commonly owned U.S. applications Ser. No. 07/430,851 filed Nov. 2, 1989, now U.S. Pat. Pat. No. 5,151,019 Ser. No. 07/744,350 filed Aug. 13, 1991, now U.S. Pat. No. 5,154,700 and Ser. No. 07/775,449 filed Oct. 15, 1991, which are hereby incorporated by reference into the present application.

2. Discussion of Background

In pumping applications involving intravenous supply of fluids it is common for deformable tubing, such as p.v.c. tubing, to be used to deliver the required fluid to the point of application. Where the supply rate and pressure is required to be carefully controlled, as is generally the case in medical applications, a serious problem can arise if the delivery tubing is restricted in any way (for example, by a patient rolling over onto it). Means can be provided to detect the resultant increase in pressure in the delivery tubing and disable the pumping action. However, if the restriction is removed (in the example given, by the patient rolling over again, off the tubing, or more likely by a nurse responding to an alarm also initiated by the means for detecting the increase in pressure) an undesirable surge of fluid to the point of application can result due to pressure retained in the delivery tubing.

SUMMARY OF THE INVENTION

Accordingly, one object of this invention is to provide a new and improved pumping arrangement in which the undesirable surge of fluid to the point of application, characteristic of the conventional pumping arrangement, is mitigated.

The above object, and others, are achieved according to the present invention by providing a novel pumping arrangement including means for subjecting fluid to pressure, input and output controllable valve means for restricting fluid flow provided on input and output sides of the fluid pressure subjecting means, means responsive to fluid pressure in delivery tubing connected in operation between the output controllable valve means and the point of application of the required fluid for detecting an increase in fluid pressure, and means responsive to increases in pressure detected by said fluid pressure responsive means for controlling both the input and output controllable valve means to open, whereby fluid under excess pressure in the delivery tubing is released back towards a source of fluid connected in operation to the input controllable valve means.

Normally means are also provided for disabling the fluid pressure subjecting means in response to increases in pressure detected by the fluid pressure responsive means.

Preferably the controllable valve means each includes means operable to squeeze the tubing to produce occlusion.

Preferably the pumping arrangement is also in accordance with the invention described in the above cross-referenced copending application Ser. No. 07/430,851, now U.S. Pat. No. 5,151,019.

Preferably again the fluid pressure responsive means includes a device as described in the above cross-referenced related co-pending application Ser. No. 07/744,350 which has issued as U.S. Pat. No. 5,154,700.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
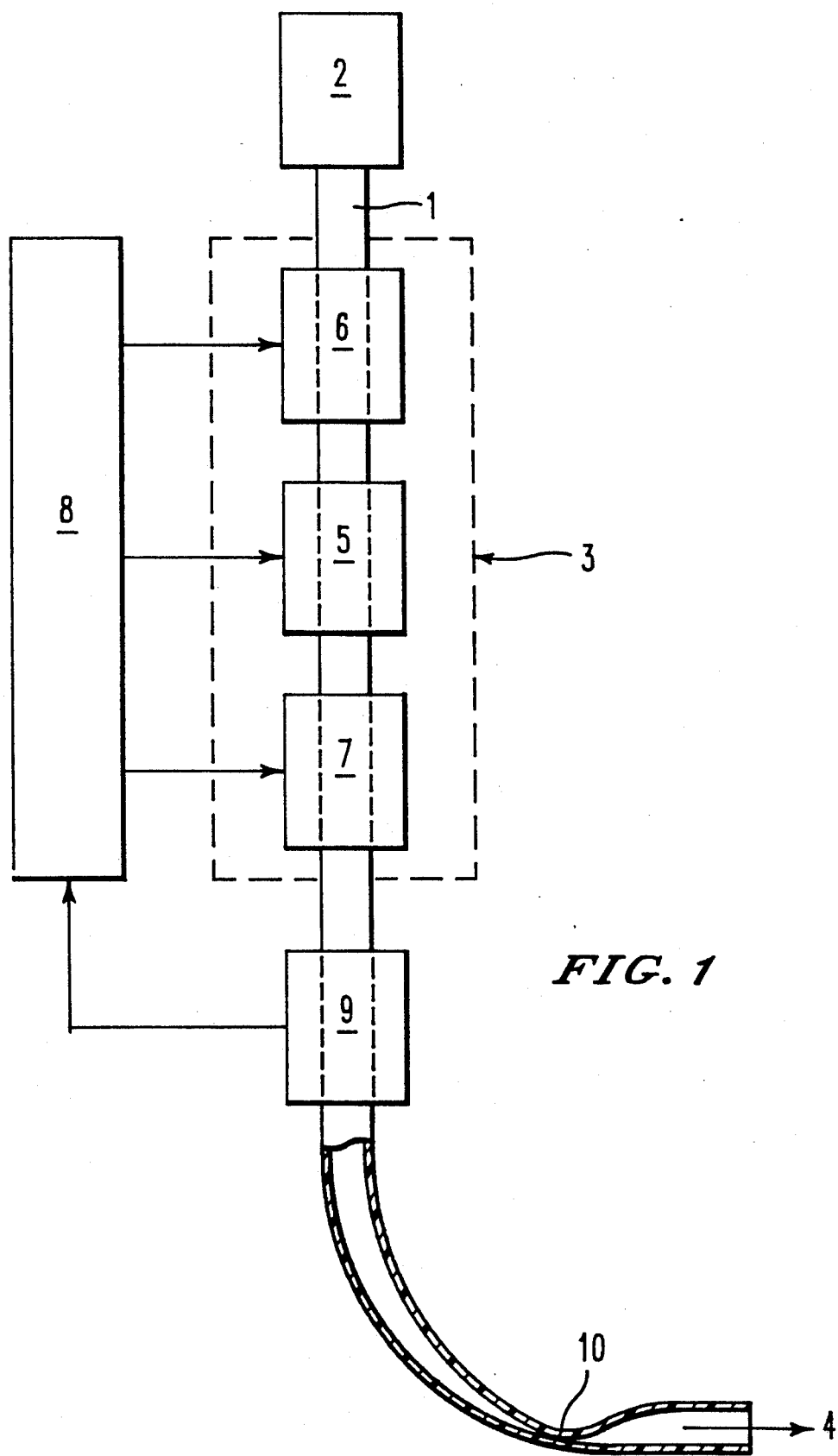
FIG. 1 is a schematic block diagram of a pumping arrangement in accordance with the present invention.

Referring to the drawing, a length of standard pliant p.v.c. tubing 1 of approximately 4.1 mm outside diameter and 0.5 mm wall thickness is connected at one end to a source of fluid 2. From that end, tubing 1 passes through a pumping device 3 to a point of application 4. The point of application in this case is a patient and the fluid is a fluid required to be supplied intravenously. The means at the point of application for achieving this is not represented, but may be taken to be conventional.

Between the source of fluid 2 and pumping device 3 the tubing 1 may be regarded as supply tubing, whilst between pumping device 3 and the point of application 3 the tubing 1 may be regarded as delivery tubing, although in this example the length of tubing is continuous.

Pumping device 3 includes a squeezing device 5 through which tubing 1 passes. Squeezing device 5 is arranged to deform tubing 1, first in one direction locally to reduce its volume and thereafter in another direction tending to restore the original cross-sectional shape of the tubing 1.

On the supply or input side of squeezing device 5 is a controllable input valve 6 which is operable to block the passage of fluid between the squeezing device 5 and the fluid source 2 by squeezing tubing 1 to produce occlusion.

On the delivery or output side of squeezing device 5 is a controllable output valve 7 which is operable to block the passage of fluid between the squeezing device 5 and the point of application 4.

For more detail of the pumping device 3 reference may be made to the specification of co-pending application Ser. No. 07/430,851 now U.S. Pat. No. 5,151,019. Squeezing device 5 and controllable valves 6 and 7 described herein corresponding to squeezing device 2 and inlet and outlet valves 3 and 4 described in detail in the specification of the co-pending application Ser. No. 07/430,851 now U.S. Pat. No. 5,151,019.

Squeezing device 5 and inlet and outlet valves 6 and 7 shown in the accompanying drawing are controlled by a microprocessor control unit 8 corresponding to control unit 52 as described in co-pending application Ser. No. 07/430,851 now U.S. Pat. No. 5,151,019 to produce pumping action as described in detail therein. Briefly, with squeezing device 5 relaxed, output valve 7 closed and inlet valve open, fluid passes into the region of the tubing encompassed by squeezing means 5. With squeezing means 5 activated locally to reduce the volume of tubing 1, inlet valve 6 closed and outlet valve 7 open, fluid is passed towards the point of application 4. The process then repeats. Normally, it will be noted, inlet valve 6 is shut when outlet valve 7 is open and vice versa.

Beyond outlet valve 7 is a pressure responsive device 9 which in this particular case is an adaptation of the pressure responsive device described in detail in the specification of co-pending application Ser. No. 07/744,350 now U.S. Pat. No. 5,154,700. Pressure responsive device 9 is connected to microprocessor control unit 8. When the signal from pressure responsive device 9 exceeds a given threshold indicating that the pressure in the delivery portion of tubing 1 had risen beyond a predetermined value indicative of a restriction caused, by the patient rolling over onto the tubing 1, control unit 8 acts to cause squeezing device 5 to be disabled and both input and output valves to be opened together so as to enable excess fluid in the delivery portion of tubing 1 to pass back towards the fluid source 2 and thus relieve the excess pressure caused by the restriction. At the same time an alarm is caused to be activated to call the attention of a nurse to the restriction.

It will be appreciated that the arrangement may be such that normal operation of the pumping device 3 recommences as pressure in the delivery portion of tubing reduces. In that case, however, "hunting" may occur since a reduction in pressure will occur not only because of a removal of the causative restriction, but also by the very opening of valves 6 and 7 upon device 9 detecting an increase in pressure.

If "hunting" as described is undesirable, renewed pumping may be subject to a reset control, operable by the nurse upon removing the cause of the restriction.

Figure 3:
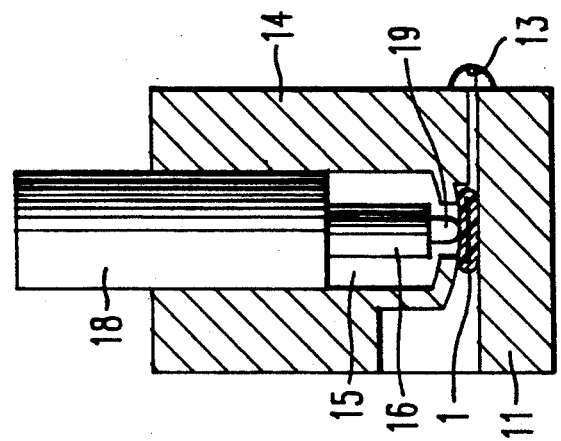
FIG. 3 is a cross-sectional view along the line x—x in FIG. 2.
Figure 2:
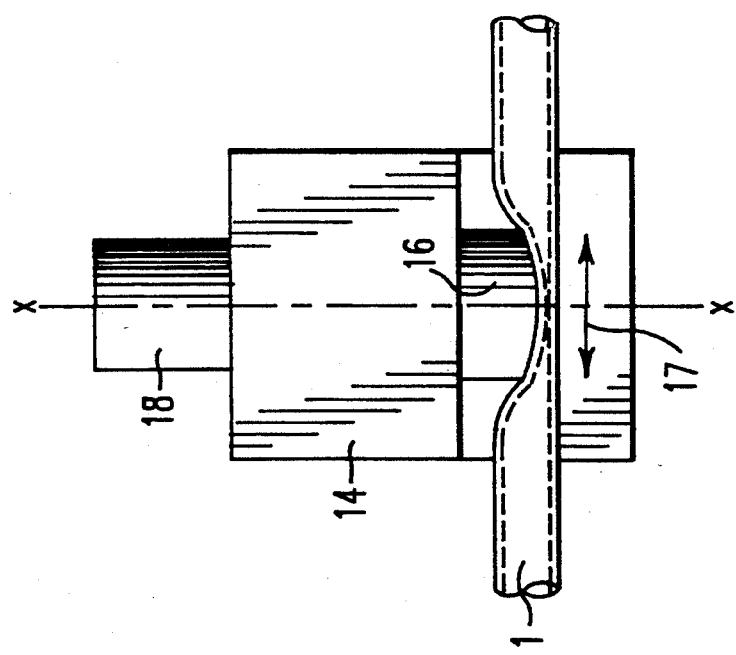
FIG. 2 is a view in elevation of one pressure responsive device in accordance with the present invention.

FIGS. 2 and 3 illustrate details of the pressure responsive device 9, as disclosed in the noted related U.S. Pat. No. 5,154,700. As shown in FIGS. 2 and 3, the device 9 includes a hard bed member 11 across the surface of which may be positioned a length of the pliant tubing 1.

Hinged to the bed member 11 by hinge 13 is a main body 14 which has a circular cylindrical passage 15 extending orthogonally away from the surface of the bed member 11 across which the tubing 1 is positioned. The passage 15 exits from main body member 14 towards tubing 1 through a tubular projection 16 which, when the main body member 14 is closed up towards the bed member 11, flattens the tubing 1 against the surface of the bed member 11 over a short length 17 thereof. The extent to which tubular projection 16 projects towards bed member 11 is such that when the main body member 14 is fully closed up to the bed member 11 (and held by means of a suitable catch, not represented) the tubing 1 is flattened against the bed member 11 without occlusion occurring and without unduly impeding the flow of liquid through the tubing 1.

Inserted within the passage 15 is a linear voltage displacement transducer 18 of known form. As know per se transducer 18 has a spring-loaded plunger 19 and produces an output digital voltage signal which is indicative of the extent to which plunger 19 extends beyond the body of the transducer 18. The output voltage signal of transducer 18 will thus vary with the displacement of a surface against which plunger 19 is pressed in the direction of action of the plunger 19.

Transducer 18 is entered into and fixed within the passage 15 to an extent such that plunger 19 is spring-biased against the flattened surface of the tubing 1 when the main body member 14 is closed up and secured to the bed member 11, as previously described.

In operation, any variation in the pressure of fluid passing through the tubing 1 will tend to cause expansions and contractions. It is believed that flattening the tubing as above described magnifies the resultant displacement of the relatively flat portion of the wall of the tubing with which the plunger 9 is in contact, thus enabling the transducer 8 to respond to such variations with a higher degree of sensitivity than would otherwise be the case.

Figure 4:
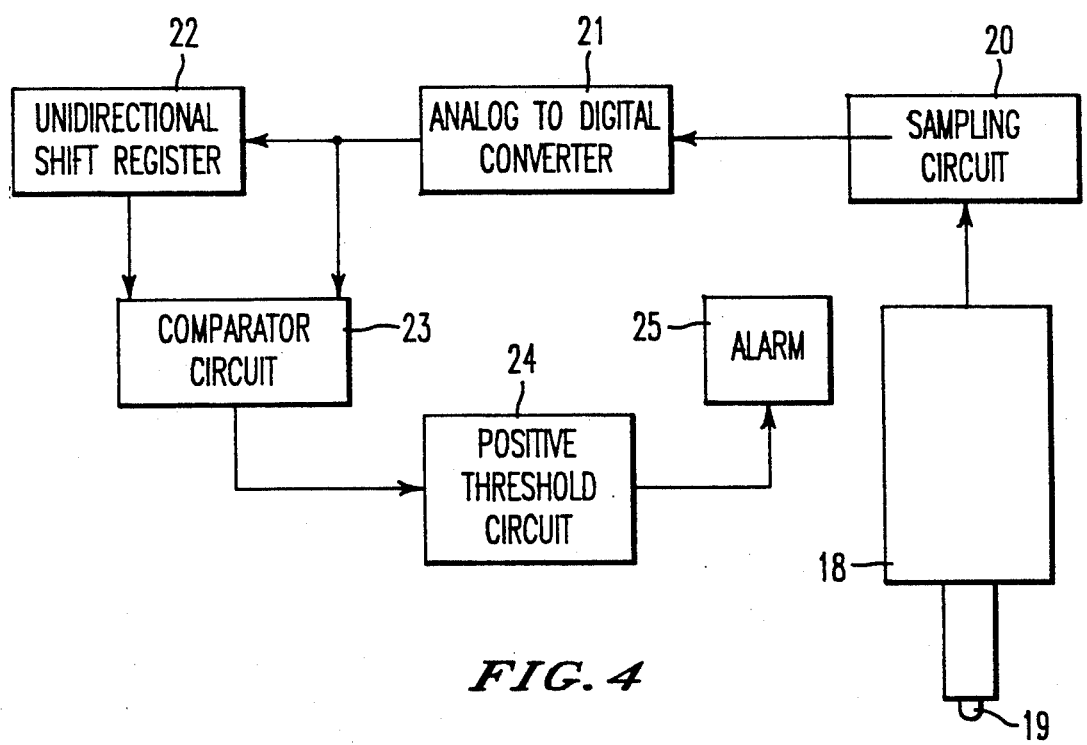
FIG. 4 is a schematic block diagram of a liquid flow monitoring arrangement associated with the pressure responsive device of FIGS. 2 and 3 in accordance with the present invention.

FIG. 4 is a schematic block diagram illustrating functional operation of the pressure responsive device 9 in conjunction with the microprocessor 8 of the present invention.

Referring to FIG. 4 only transducer 18 and plunger 19 of the pressure responsive device 9 of FIGS. 2 and 3 are represented. The analog output voltage of transducer 18 is arranged to be sampled at the rate of once per second by a sampling circuit 20.

The output of sampling circuit 20 is connected to the input of an analog-to-digital converter 21.

The output of analog-to-digital converter 21 is connected to a unidirectional "count down" only shift register 22, where it is stored, and in parallel to one input of a comparator circuit 23. A second input for comparator circuit 23 is derived from the output of shift register 22 so that comparator circuit 23 compares the digital signal output of analogue-to-digital converter 21 derived from one sample taken by sampling circuit 20 with that derived from the sample taken one second before.

The output of comparator circuit 23 is connected via a positive threshold circuit to a suitable visual and/or aural alarm 25.

For a further understanding of the operation of the arrangement illustrated in FIG. 4 reference is made to the above-noted U.S. Pat. No. 5,154,700.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letter patent of the United States is:

1. A pumping arrangement comprising:
   means for subjecting fluid to pressure;
   input and output controllable valve means for restricting fluid flow provided on a respective input and output side of said subjecting means;
   means responsive to fluid pressure in delivery tubing connected in operation between the output controllable valve means and the point of application of the required fluid for detecting an increase in fluid pressure; and
   means responsive to increases in pressure detected by said fluid pressure responsive means for controlling both said input and output controllable valve means to open, whereby fluid under excess pressure in said delivery tubing is released back towards a source of fluid connected in operation to said input controllable valve means.

2. An arrangement as claimed in claim 1, wherein said input and output controllable valve means each comprise:
   means operable to squeeze said tubing to produce occlusion.

3. An arrangement as claimed in claim 1, further comprising:
   means for disabling said fluid pressure subjecting means in response to increases in pressure detected by said fluid pressure responsive means.

4. An arrangement as claimed in claim 3, wherein said input and output controllable valve means each comprise:
   means operable to squeeze said tubing to produce occlusion.

5. An arrangement as claimed in claim 1, wherein:
   said means for subjecting fluid to pressure comprises means for deforming tubing in which said fluid flows, thereby to reduce the volume of said tubing, said deforming means including,
   means for first deforming said tubing in one direction, and means for then deforming said tubing in an other direction which tends to restore the original cross-sectional shape of said tubing; and
   said means for controlling said input and output controlled valve means controls said valve means to open and close in synchronism with deforming of said tubing so that liquid is displaced from an outlet side of said tubing without pressurization of liquid in said tubing as a function of change of volume of the tubing during deformation.

6. An arrangement as claimed in claim 5, wherein said fluid pressure responsive means comprises:
   means for causing tubing in which said fluid flows to assume an elongate cross-section over a length thereof;
   means for applying pressure to an area in a relatively flattened region of the wall of said tubing within said length and responsive to movement thereof to provide indications of variations in the pressure of said fluid; and
   means for compensating for movement of said area occurring after said pressure is applied thereto and due to other than variations in the pressure of said fluid.

7. An arrangement as claimed in claim 1, wherein:
   said means for subjecting fluid to pressure comprises means for sequentially deforming said tubing first in one direction to locally reduce the volume of said tubing and then in another direction which tends restore the original cross-sectional shape of said tubing; and
   said means for controlling the operation of said deforming means and said input and output controllable valve means such that at times when said tubing is being deformed by said deforming means to reduce the volume of tubing locally, the input valve means is in a condition of restrictive flow whilst the output valve means is in a condition of increase flow, and liquid is thereby displaced from an outlet of the tubing without pressurization of the liquid, and at times when said volume is being locally restored, the output valve means is in a condition of restricted flow while the input valve means is in a condition of increased flow.

8. An arrangement as claimed in claim 7, wherein said fluid pressure responsive means comprises:
   means for causing tubing in which said fluid flows to assume an elongate cross-section over a length thereof;
   means for applying pressure to an area in a relatively flattened region of the wall of said tubing within said length and responsive to movement thereof to provide indications of variations in the pressure of said fluid; and
   means for compensating for movement of said area occurring after said pressure is applied thereto and due to other than variations in the pressure of said fluid.

9. An arrangement as claimed in claim 1, wherein said fluid pressure responsive means comprises:
   means for causing tubing in which said fluid flows to assume an elongate cross-section over a length thereof;
   means for applying pressure to an area in a relatively flattened region of the wall of said tubing within said length and responsive to movement thereof to provide indications of variations in the pressure of said fluid; and
   means for compensating for movement of said area occurring after said pressure is applied thereto and due to other than variations in the pressure of said fluid.

10. An arrangement as claimed in claim 9, wherein said compensating means comprises:
    means for comparing an indication derived at a given point in time with an indication derived at a previous point in time; and
    means responsive to the extent of any difference therebetween for signalling that a change in the pressure of said fluid has occurred.

11. An arrangement as claimed in claim 10, wherein the indications are produced by means for sampling at regular intervals from the time that pressure is first applied to said area and continuing beyond the point in time at which the aforementioned stable state is reached.

12. An arrangement as claimed in claim 11, comprising:
    means for comparing an indication produced by sampling with an immediately preceding indication produced by sampling.

13. An arrangement as claimed in claim 11, wherein the rate of sampling is approximately once per second.

14. An arrangement as claimed in claim 9, wherein said means for causing said tubing to assume an elongate cross-section over a length thereof comprises:
    a bed member having a non-resilient substantially flat surface across which said tubing may be positioned;
    means for flattening said tubing non-occlusively over a length thereof against said surface of said bed member; and
    means for applying pressure to a point in a relatively flattened region of the wall of said tubing within said length and responsive to movement thereof to provide an indication of such movement.

15. An arrangement as claimed in claim 14, wherein said means for applying pressure comprises:
    a linear voltage displacement transducer having a spring-loaded plunger and producing, in operation, an output voltage signal which is indicative of the extent to which said plunger extends beyond the body of said transducer, said plunger being arranged to be pressed into the relatively flattened region of the wall of said tubing at said point.

16. An arrangement as claimed in claim 15, wherein said body member and said bed member are hinged together and means are provided for securing the one to the other when the body member is closed up to said bed member in operation.

17. An arrangement as claimed in claim 13, wherein the output of said linear voltage displacement transducer is arranged to be sampled by a sampling circuit the output of which is connected via an analog-to-digital converter to the input of a unidirectional shift register and in parallel to one input of a comparison circuit a second input for which is derived from the output of said shift register whereby the digitalized output of said sampling circuit is compared with the immediately preceding output of said sampling circuit outputted from said shift register, the output of said comparison circuit being connected via a threshold circuit to operate a suitable alarm.

18. An arrangement as claimed in claim 17, wherein the constituents connected to take output from said linear voltage displacement transducer and operate said alarm are embodied as a suitably programmed microprocessor.

19. An arrangement as claimed in claim 15, wherein said transducer is housed in a body member which is arranged to be moved towards and away from said bed member whereby said tubing may be engaged or released by said plunger.

20. An arrangement as claimed in claim 19, wherein said body member comprises:
a tubular projection extending beyond a cylindrical passage within said body member, said passage opening in a surface of said body member facing said bed member and said tubular projection serving to flatten said tubing as aforesaid as said body member is moved towards said bed member.

* * * * *